United States Patent
Barthold et al.

(10) Patent No.: US 10,485,649 B2
(45) Date of Patent: Nov. 26, 2019

(54) MODULAR STENTGRAFT SYSTEM

(71) Applicant: JOTEC GMBH, Hechingen (DE)

(72) Inventors: Franz-Peter Barthold, Balingen (DE); Thomas Bogenschuetz, Hechingen-Stein (DE)

(73) Assignee: JOTEC GMBH, Hechingen (DE)

(*) Notice: Subject to any disclaimer, the term of this patent is extended or adjusted under 35 U.S.C. 154(b) by 61 days.

(21) Appl. No.: 15/586,094

(22) Filed: May 3, 2017

(65) Prior Publication Data

US 2017/0231751 A1    Aug. 17, 2017

Related U.S. Application Data

(63) Continuation of application No. PCT/EP2015/075631, filed on Nov. 3, 2015.

(30) Foreign Application Priority Data

Nov. 4, 2014 (DE) ...................... 10 2014 116 012.6

(51) Int. Cl.
*A61F 2/07* (2013.01)
*A61F 2/852* (2013.01)
(Continued)

(52) U.S. Cl.
CPC ................ *A61F 2/07* (2013.01); *A61F 2/852* (2013.01); *A61F 2/89* (2013.01); *A61F 2/91* (2013.01);
(Continued)

(58) Field of Classification Search
CPC ...... A61F 2/06; A61F 2/07; A61F 2/82; A61F 2/89
See application file for complete search history.

(56) References Cited

U.S. PATENT DOCUMENTS 8,636,791 B1    1/2014  Raju et al.
9,192,491 B1 *  11/2015 Raju ....................... A61F 2/852
(Continued)

FOREIGN PATENT DOCUMENTS

DE            60019788 T2     1/2006
DE      10 2012 100839 A1     8/2013
(Continued)

OTHER PUBLICATIONS

International Preliminary Report for Patentability for PCT/EP2015/075631, dated May 18, 2017, 18 pages (Including English Translation).
(Continued)

*Primary Examiner* — Jason-Dennis N Stewart
(74) *Attorney, Agent, or Firm* — Rimon, P.C.

(57) ABSTRACT

The present invention relates to a stent-graft system comprising a first hollow cylindrical stent-graft body and at least one second hollow cylindrical stent-graft body. The first and the second stent-graft bodies are two structurally separate stent-graft bodies, and each comprise a first end, a second end, and a longitudinal axis. The first and the second stent-graft bodies further each comprise a stent-graft portion and a stent portion. The stent portion of the first stent-graft body and the stent portion of the second stent-graft body are designed in such a way that they can be at least partially inserted into one another in order to form one shared stent portion which is free from prosthesis material.

22 Claims, 4 Drawing Sheets

(51) Int. Cl.
    *A61F 2/89*     (2013.01)
    *A61F 2/91*     (2013.01)
    *A61F 2/90*     (2013.01)
    *A61F 2/06*     (2013.01)

(52) U.S. Cl.
    CPC ........... *A61F 2/90* (2013.01); *A61F 2002/061* (2013.01); *A61F 2002/075* (2013.01); *A61F 2210/0014* (2013.01); *A61F 2230/0054* (2013.01); *A61F 2230/0069* (2013.01); *A61F 2250/006* (2013.01); *A61F 2250/0063* (2013.01)

(56) References Cited

U.S. PATENT DOCUMENTS

2009/0036977 A1\* 2/2009 Rassat ................. A61F 2/07
                                                      623/1.42

2010/0312326 A1   12/2010   Chuter et al.
2014/0336749 A1   11/2014   Bogenschuetz et al.

FOREIGN PATENT DOCUMENTS

| EP | 1 177 780 A2 | 2/2002 |
| EP | 1 759 666 A1 | 3/2007 |
| WO | WO 2001/035864 A1 | 5/2001 |
| WO | WO-2008/130572 A1 | 10/2008 |
| WO | WO 2010/150208 A2 | 12/2010 |

OTHER PUBLICATIONS

International Search Report for PCT/EP2015/075631, dated Jan. 25, 2016, 8 pages (Including English Translation).

\* cited by examiner

MODULAR STENTGRAFT SYSTEM

CROSS REFERENCES TO RELATED APPLICATIONS

This application is a continuation of international patent application PCT/EP2015/075631, filed on Nov. 3, 2015, designating the U.S., which international patent application has been published in German language and claims priority from German patent application DE 10 2014 116 012.6, filed on Nov. 4, 2014. The entire contents of these priority applications are incorporated herein by reference.

BACKGROUND OF THE INVENTION

The present invention relates to a modular stent-graft system for delivery into a blood vessel of a patient to be treated.

Vascular implants of this type are known in the prior art, for example from DE 103 37 739.5.

In general, it is known to utilize intraluminal vascular implants, which are also referred to as endovascular stents or stent grafts, for treating weakened, injured, torn, or aneurysmal vessels. For this purpose, a vascular implant or stent graft is released at the diseased or injured site of the vessel, and restores the functionality of the original vessel and/or supports the remaining vascular integrity.

In this case, an aneurysm is understood to mean an expansion or bulging of an arterial blood vessel as a result of congenital or acquired changes in the wall. The bulging can involve the vascular wall in entirety or, as in the case of a so-called false aneurysm or so-called dissection, blood from the lumen of the vessel collects between the layers of the vascular wall and separates said layers. In the advanced stage of the non-treatment of an aneurysm, the artery can rupture, with the consequence that the patient bleeds internally.

The self-expanding vascular implants utilized for treating aneurysms of this type generally consist of a hollow cylindrical metal frame or scaffold, the lateral face of which is covered by a textile foil or polymer foil, and therefore a hollow cylindrical body results. For implantation, the vascular implant is radially compressed, and therefore its cross-sectional area is substantially reduced. With the aid of a delivery system, the vascular implant is then brought into the region of the aneurysm, where it is released. Due to the spring action of the metal frame/scaffold, the vascular implant expands back into its original shape and thereby deploys its lateral face which lodges internally in the blood vessel, proximally and distally to the aneurysm. In this way, the blood now flows through the vascular implant and a further strain on the bulge is prevented.

The metal frame of such vascular implants usually consists of, for example, a wire mesh or so-called stent springs which are successively arranged and spaced apart from one another over its longitudinal axis and which circumferentially meander, and which are optionally interconnected via connection supports made from wire, or which are indirectly interconnected merely via the implant material. The wire mesh or the stent springs are usually made from a shape memory material, usually Nitinol, whereby, after insertion into a vessel in order to be released, the stent springs transition back into the expanded state and thereby "deploy" the vascular implant.

Aneurysms frequently occur in the region of the abdominal aorta (Aorta abdominalis) or the thoracic aorta (Aorta thoracica). In order to treat aneurysms in the abdominal aorta or the thoracic aorta, it is already known to stabilize the artery via implantation of a stent to the extent that a rupture of the vessel is avoided.

Aneurysms can also occur, however, in the so-called ascending branch of the aorta (Aorta ascendens). The ascending branch of the aorta is directly connected to the heart. Proceeding from the root of the aorta (Sinus aortae), the ascending branch extends, in a slightly curved shape, upward and away from the heart and, there, transitions into the aortic arch (Arcus aortae). In the region of the aortic arch, the head vessels branch off, e.g., the left common carotid artery and the right common carotid artery. The aortic arch extends in a curve through approximately 180° with a very narrow radius and connects the ascending branch of the aorta to the thoracic artery and, further along, to the abdominal artery.

It is important—not only in the region of the aortic arch—to avoid blocking lateral vessels that branch off from main vessels by the positioning of the vascular implant, and therefore many vascular implants have open zones or so-called fenestrations, via which lateral branches, which branch off from the vascular implant and protrude into the lateral vessels, can be inserted and fixed on the vascular implant.

An aneurysm or a dissection in the ascending branch of the aorta is treated, even today, in an invasive open surgical procedure. So far, such an operation regularly necessitates two major surgeries carried out at different times, and is a very large and complex and, therefore, dangerous surgical operation, since a hypothermic perfusion, i.e., an artificial, cold, extracorporeal circulation, or a hypothermic circulatory arrest must be carried out not only on the heart, but also on the brain and the abdominal organs of the patient. Only a few cardiac surgeons at experienced hospitals are familiar with such a surgical procedure.

There is still a great demand for stent systems and stent-graft systems, or vascular implants, with the aid of which the above-described surgical procedure could be simplified and shortened.

SUMMARY OF THE INVENTION

Therefore, it is an object of the present invention to provide a system, by means of which aneurysms, in particular in the region of the ascending aorta, the aortic arch, and the descending aorta, can be treated rapidly and in an uncomplicated manner, and which also enables less experienced cardiac surgeons to carry out the above-described surgical procedures.

According to the invention, this problem and other problems are solved by a stent-graft system comprising a first hollow cylindrical stent-graft body and at least one second hollow cylindrical stent-graft body, wherein the first and the second stent-graft bodies are structurally separate from one another, and wherein the first and the second stent-graft bodies each have a first end, a second end, and a longitudinal axis, wherein the first and the second stent-graft bodies each comprise a stent-graft portion which is formed from a stent-graft scaffold and a prosthesis material applied thereon, wherein the first and the second stent-graft bodies each further comprise a stent portion which is formed from a stent scaffold which is free from prosthesis material and comprises a first and a second stent-portion end, wherein the stent portion is fixedly connected via its first stent-portion end to the stent-graft portion in each case, and wherein the stent portion of the first stent-graft body and the stent portion of the second stent-graft body are designed in such a way that they can be at least partially inserted into one another via their respective second stent-portion ends in order to form one shared stent portion which is free from prosthesis material.

The problem addressed by the invention is solved in entirety in this manner.

By way of the new stent-graft system, a portion free from prosthesis material can be created in an easy way, via which the branching-off vessels can continue to be supplied with blood, wherein the injured vessels in question are simultaneously supported by the so-called covered stent-graft portion, i.e., the portion having the prosthesis material. The delivery and placement of this system can be handled precisely and easily due to the two-pieced design of said system.

In this case, the one module of the stent-graft system, i.e., the first hollow cylindrical stent-graft body, is initially inserted and correctly placed in such a way that vessels branching off from the main vessel are located in the stent portion that is free from prosthesis material, and the second module is subsequently inserted into the blood vessel to be treated and partially into the first module in such a way that the two stent portions that are free from prosthesis material at least partially overlap. The second module, which is the last to be inserted, or its portion that is free from prosthesis material, therefore expands within the portion of the first module that is free from prosthesis material and thereby anchors the second module, i.e., the second hollow cylindrical stent-graft body, partially within the first hollow cylindrical stent-graft body. The portions of the second module, or the second hollow cylindrical stent-graft body, that are not anchored within the stent portion of the first module that are free from prosthesis material expand in the vessel to be treated and rest against its vessel walls.

Due to the stent-graft system according to the invention, i.e., due to the combination of two individual modules which are structurally separate from one another and are to be inserted one after the other, and each of which comprises a short, so-called "covered" stent-graft portion which is covered with prosthesis material, and a so-called "non-covered" stent portion which lies between these covered stent-graft portions in the expanded and released state and which is free from prosthesis material, it is also possible, for example, during an implantation in the aortic arch, to simultaneously treat the three sections of the aorta, i.e., the Aorta ascendens (ascending aorta), the aortic arch, and the descending aorta (descending main aorta). Therefore, it is possible to dispense with the resection of the aortic arch and all the associated complex perfusion requirements for the brain and the lower body, and the procedure can be carried out merely by separating the uppermost section of the ascending aorta in a short, approximately 10-to-20-minute long selective head perfusion phase or a hypothermic arrest phase in order to deliver and release the new vascular prosthesis. The delivery and release can take place easily in this case under the view of the human eye or an angioscope.

According to the invention, an intraluminal vascular prosthesis is provided for the first time, by means of which the possibility is created for surgically simplifying operations, in particular, on the aortic arch or in the ascending aorta, on the aortic arch and the descending aorta, and to substantially shorten said operations. Advantageously, it is therefore possible for the above-described operations on the aortic arch to be carried out not only by highly specialized cardiac surgeons. Furthermore, the vascular prosthesis according to the invention can also be utilized with very sick patients and with elderly patients who have aortic wall layers that are damaged, e.g., due to age, and with non-perfusion of vital organ systems such as the brain or abdominal organs, since these can be inserted in a shortened and surgically simplified method.

Advantageously, the stent portion that is free from prosthesis material is released in the expanded state in the region of the aortic arch. As a result, it is ensured that the blood flow in the branching-off vessels, such as the Truncuns brachiocephalicus, the left Aorta carotis communis, and the left Arteria subclavia, is not adversely affected. The blood flowing through the aortic arch and the vascular prothesis/stent-graft system to be anchored therein can flow out of these by passing through the openings in the vascular prosthesis which are present in the uncovered stent portion; it is simultaneously ensured that the stent-graft system is securely anchored in the vessel via the stent-graft portions which then lie, in the released state of both modules, to the left and the right of the shared, formed, uncovered stent portion; this can be achieved, on the one hand, via radial expansion forces of the stent-graft portions and the resultant resting of the vascular prosthesis against the vascular wall in these regions. If necessary, or if so desired, this fixation can also be achieved by suturing the stent-graft portion to the aortic wall, in which case, according to one specific embodiment, the stent-graft portion does not have circumferentially meandering rings and supports, or only optionally comprises such rings and supports.

Some of the terms used herein are defined in greater detail in the following, even though said terms are clearly understood by a person skilled in the art per se and with reference to the present disclosure:

In the present case, a "stent spring" as discussed at the outset is understood to be any one-piece, annular element which can be compressed due to its material and which can expand again in a springy manner after the compression pressure is removed. The expression "meandering" is understood to mean, in this case, any loop-shaped or sinus-curved course of the stent springs or of the stent wire, wherein every stent spring is formed as one piece, i.e., from a circumferentially meandering stent spring ring, or in other words, from a stent spring ring following a wavy peripheral path.

In this context, a "one-piece stent spring following a wavy peripheral path" or a "one-piece stent spring circumferentially meandering" is an annular stent element which is expandable and compressible in a springy manner and which has a wavy circumference, wherein one wave crest and one wave trough, which form one phase, are present in alternation.

Advantageously, a pointed arch is formed in each case from two legs and one maximum point or one minimum point lying between the legs.

In the present case, "at least one pointed arch" means that the lateral body is billowed by way of a single pointed arch of a stent spring being flared, or by way of two or more pointed arches. In one preferred embodiment, two pointed arches of one stent spring are flared. In principle, the plurality of pointed arches circumferentially meandering form the stent spring of the main body, and the flared pointed arch or arches form the branching-off point for the lateral body.

In principle, in the case of stent grafts or endoluminal prostheses, the terms "distal" and "proximal" are used in general and in the present case for describing the particular ends, wherein the term "distal" describes the part or the end lying further downstream with respect to the blood flow. The term "proximal", however, describes a part or the end lying further upstream with respect to the blood flow. In other words, the term "distal" means the direction of the blood flow, and the term "proximal" means the direction opposite to the blood flow. In the case of catheters, however, or in the case of delivery systems, the term "distal" refers to the end of the catheter or delivery system that is inserted into the patient or that lies furthest away as viewed by the user, and the term "proximal" refers to the end that is located closer to the user.

Therefore, the "proximal" and the "distal" openings of the vascular implant in the present case are the openings through which the blood flow through the hollow cylindrical body of the vascular implant is ensured: If the vascular implant according to the invention is implanted in a blood vessel such as the aorta, for example, the blood coming from the heart therefore flows through the proximal opening in the vascular implant and said blood emerges from the vascular implant through its distal openings.

The stent-graft system or its two hollow cylindrical main bodies can have a uniform diameter or different diameters along their entire length in this case.

By definition, the stent springs are not directly connected to each other, and do not comprise any connecting legs or struts or similar connecting elements among themselves. The stent springs are connected to each other only via the implant material onto which the stent springs are mounted, whereby an "indirect connection" between the stent springs is created.

In the present case, a "stent" refers to any device or a structure which provides a prosthesis with an expansion force and/or a support function.

The expression "stent graft" is intended to mean in the present case, as well in the prior art, that one or several stents (or stent springs) and an implant ("graft") connected thereto comprise material which forms a lumen through at least one portion of the prosthesis.

According to one embodiment of the stent-graft system, it is preferred when the scaffold of the stent-graft portion of the first and/or the second stent-graft body is formed from stent springs which are disposed and spaced apart from one another n the longitudinal direction of said scaffold, and each of which circumferentially meanders, and a prosthesis material which is fastened to the stent springs and connects said stent springs.

According to one further embodiment, the scaffold of the stent-graft portion and of the stent portion of the first and/or second stent-graft body are formed as one piece, and the prosthesis material in the stent-graft portion is applied thereon as coating foil.

In this context, it is preferred when the prosthesis material comprises a material which is selected from a textile or a polymer.

In particular, it is preferred when the prosthesis material comprises a material or is made from said material which is selected from polyester, polyurethane, polystyrene, polytetrafluoroethylene, ultra-high-molecular-weight polyethylene (UHMPE), or mixtures thereof.

The prosthesis material of the first and the second stent-graft bodies can be the same or different in this case.

According to one embodiment of the stent-graft system according to the invention, it is preferred when the stent-graft system is designed for implantation into an aorta, in particular in the region of the ascending aorta, the aortic arch, and the descending aorta, wherein the stent-graft system can be transferred from a compressed state into an expanded state for insertion into the aorta, and wherein the first and the second stent-graft bodies are designed for anchoring the stent-graft system in the aorta.

In this context, it can be provided and preferred in further embodiments when the shared stent portion which is free from prosthesis material can be released in the expanded state in the region of the aortic arch.

In the stent-graft system according to the invention, it is provided in this context that the covered stent-graft portion of the first stent-graft body comes to rest distally to the Arteria subclavia, and the non-covered stent portion of the first stent-graft body comes to rest in the aortic arch. The covered stent-graft portion of the second stent-graft body is placed in the proximal aortic arch.

In other words, the stent-graft portion of the first stent-graft body is therefore located at the distal end region of the stent-graft system and can therefore also be referred to as the distal stent-graft portion in the assembled form of the two stent-graft bodies; the stent-graft portion of the second stent-graft body is located at the proximal end region of the vascular prosthesis, which therefore forms—in the assembled state of the two stent-graft bodies as well—a proximal stent-graft portion.

In the released state, in which the two individual stent-graft bodies are anchored by means of a partial overlap of the particular stent portions with one another, the two covered stent-graft portions therefore form the outer ends of the assembled vascular prosthesis, wherein the stent-graft portion of the first stent-graft body is thereby provided at the distal end of the vascular prosthesis, which is now in its assembled state, and the stent-graft portion of the second stent-graft body is provided at the proximal end.

According to one preferred embodiment, it is provided that the stent-graft portion and the stent portion of the first and/or the second stent-graft body are made from a self-expanding material or comprise such a material. In this case, it is preferred in particular that the material is Nitinol.

According to yet another preferred embodiment, the stent-graft portion of the first and/or the second stent-graft body comprises between two, three, four and five, preferably three stent springs which are made from supports which circumferentially meander and are arranged behind one another. These rings are connected to each other via the prosthesis material. According to one preferred embodiment, the supports or stent springs themselves are not connected to each other via struts or the like, or are not in direct contact with each other. This embodiment has the advantage that a person skilled in the art can adjust the length of the stent-graft portion to the particular circumstances of the vessel.

Furthermore, it is provided according to yet another embodiment that the stent portion of the first and/or the second stent-graft body that is free from prosthesis material comprises a woven or twisted wire mesh.

In this case, a "wire mesh" is understood to be any embodiment of a stent in which different wire strands are interwoven, intertwined, or linked in any other way such that a structure is formed that has zones, regions or points at which the strands lie over one another, and that has zones or regions that are free from the wire strands and therefore form openings or windows or meshes.

According to one alternative embodiment, the stent portion of the first and/or the second stent-graft body that is free from prosthesis material is a laser-cut tube. This embodiment as well comprises meshes or openings, via which the blood conveyed in the aorta or in the aortic arch can emerge from the aorta into the branching-off vessels, in particular the Truncus brachiocephalicus, the left Aorta carotis communis, and the left Arteria subclavia, thereby ensuring that these vessels are supplied with blood.

According to one particularly preferred embodiment, the stent-graft portion of the first and/or the second stent-graft body has a length of between approximately 20 mm and approximately 100 mm, and the particular non-covered stent portion has a length of between approximately 30 mm and approximately 100 mm. The particular stent-graft portions and stent portions of the first and the second stent-graft bodies can have different lengths which are within the scope of the ranges which were mentioned.

The present invention further relates to a method for releasing the stent-graft system according to the invention, wherein the method comprises the following steps of:

inserting the first stent-graft body into an aorta of a patient in the compressed state in such a way that the stent-graft portion of the first stent-graft body is positioned completely distally to the Arteria subclavia;

transferring the first stent-graft body into the expanded state in such a way that the stent portion of the first stent-graft body that is free from prosthesis material is released in the aortic arch in the region of the branches to the Truncus brachiocephalus, the Arteria carotis communis, and the Arteria subclavia sinistra, inserting the second stent-graft body into the aorta of a patient in the compressed state in such a way that the stent-graft portion of the second stent-graft body is positioned completely proximally to the branch to the Truncus brachiocephalus, and the stent portion of the second stent-graft body that is free from prosthesis material is at least partially inserted into the stent portion of the first stent-graft body that is free from prosthesis material; and transferring the second stent-graft body into the expanded state in such a way that the stent portion of the second stent-graft body that is free from prosthesis material is at least partially anchored in the stent portion of the first stent-graft body that is free from prosthesis material.

By means of this method, it is ensured that the stent-graft system according to the invention is positioned in such a way that the overlapping, non-covered stent portion allows the blood to flow into the branching-off vessels Truncus brachiocephalus, Arteria carotis communis, and Arteria subclavia sinistra.

In this case, care is taken to ensure that the covered stent-graft portion of the first stent-graft body terminates nearly distally to the branch to the Arteria subclavia. The non-covered stent portion is now released in the aortic arch, wherein the wire meshes or the openings in the laser-cut stent portion are so spacious that there is no danger in the sense of obstructing the branches to the head-neck vessels (Truncuns brachiocephalicus, left Aorta carotis communis, and left Arteria subclavia). Subsequent thereto, the second stent-graft body is released in such a way that its covered stent-graft portion is positioned proximally to the branch to the Truncus brachiocephalicus. Said stent-graft body expands or can be sutured to the proximal aortic arch. This method has the advantage that, if the ascending section of the Aorta ascendens had been previously replaced, e.g., has just been replaced, this bleeding-arresting suture simultaneously incorporates the vascular prosthesis.

The stent-graft system according to the invention and the method for delivery and release therefore offer the advantage that a tear or an aneurysm present in the region of the Aorta ascendens can be eliminated via resection and conventional prosthetic implantation—enabled by the stent-graft portion of the second stent-graft body—as has been done so far, and any remaining tears in the intima in the proximal Aorta descendens or in the aortic arch may be simultaneously reliably stabilized and, in fact, without the risk of rupture over the long-term. This can also be achieved, in particular, by way of designing the vascular prosthesis to be, for example, 10% to 20% larger or longer than is necessary in the particular case (so-called "oversizing").

Therefore, in particular in the case of a dissection disorder or a complex aneurysmal disorder of the thoracic aorta, the surgical complexity and amount of time required can be reduced to one-third as compared to operations and systems applied in the prior art, while achieving a comparable result, and therefore the risk of the surgical procedure can be significantly reduced.

The present invention therefore further also relates to the use of the stent-graft system according to the invention in the treatment of dissection disorders or aneurysmal disorders, in particular of the thoracic aorta.

Further advantages result from the figures and the description of preferred exemplary embodiments that follow.

It is understood that the features mentioned above and which are described below may be used not only in the combination described, but also in other combinations or alone, without leaving the scope of the present invention.

BRIEF DESCRIPTION OF THE DRAWINGS

Exemplary embodiments of the invention are represented in the drawing and are described in greater detail in the description that follows. In the Figures.

DESCRIPTION OF PREFERRED EMBODIMENTS

Figure 1:
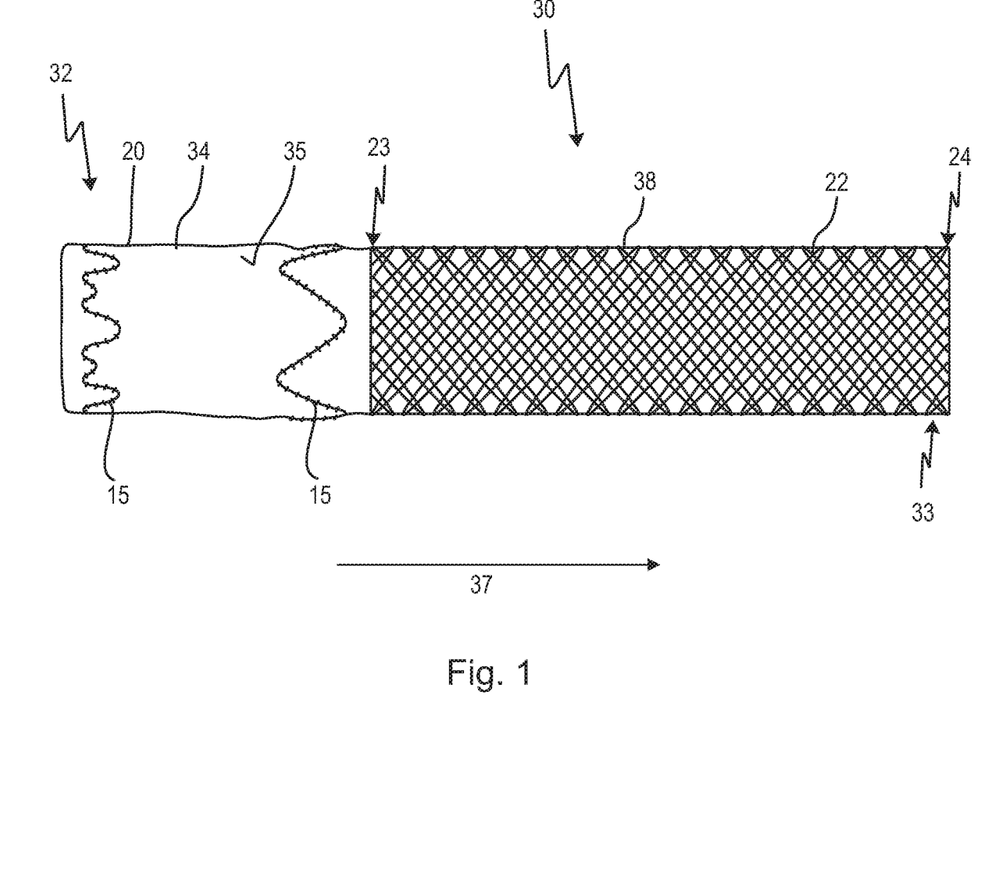
FIG. 1: shows a schematic representation of one embodiment of a first stent-graft body of the stent-graft system according to the invention (not shown to scale), in the non-inserted but expanded state.

In FIG. 1, reference numeral 30 indicates, overall, a first stent-graft body 30 of a stent-graft system 10 according to the invention, comprising a distal end 32 and a proximal end 33, and a longitudinal axis 37. The first stent-graft body 30 comprises a stent-graft portion 34 and a stent portion 38. The stent-graft portion 34, in turn, comprises a stent-graft scaffold 20 and a prosthesis material 35 applied thereon. In the embodiment shown in FIG. 1, the stent-graft scaffold 20 comprises rings or stent springs 19 which are arranged behind one another, or in other words, disposed and spaced apart successively in the longitudinal axis 37, and which meander around the circumference of the stent-graft body 30, and are indirectly interconnected via a prosthesis material 35. The stent portion 38 likewise comprises a stent scaffold 22, is free from prosthesis material, and comprises open cells or openings 40. Reference numerals 23 and 24 indicate a first and a second stent-portion end 23, 24.

Figure 2:
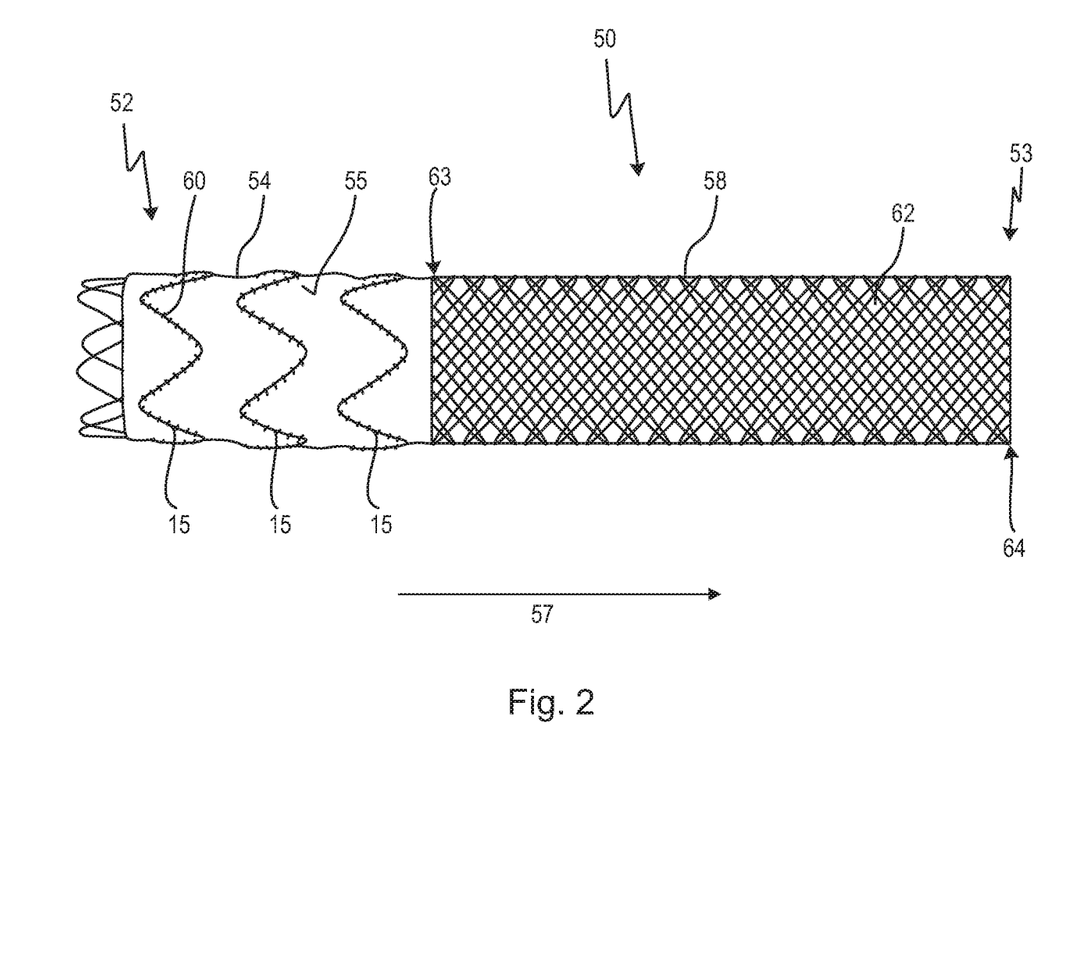
FIG. 2: shows a schematic representation of a second stent-graft body of the stent-graft system according to the invention (not shown to scale), likewise in the non-inserted but expanded state.

The embodiment of the second stent-graft body 50 shown in FIG. 2 comprises a first stent-graft-body end 52 and a second stent-graft-body end 53 and a longitudinal axis 57. Furthermore, the second stent-graft body 50 comprises a stent-graft portion 54 which, in turn, comprises a stent-graft scaffold 60, and which, in this embodiment and as in the case of the stent-graft portion 34 of the first stent-graft body 30, comprises rings or stent springs 15 which are successively arranged and spaced apart in the longitudinal direction and meander around the circumference of the stent-graft body 50. The stent-graft portion 54 is furthermore covered with a prosthesis material 55 which connects the rings/stent springs 15. The second stent-graft body 50 further comprises a stent portion 58 which is formed from a stent scaffold 62 free from prosthesis material, and comprises a first stent-portion end 63 and a second stent-portion end 64.

Figure 3:
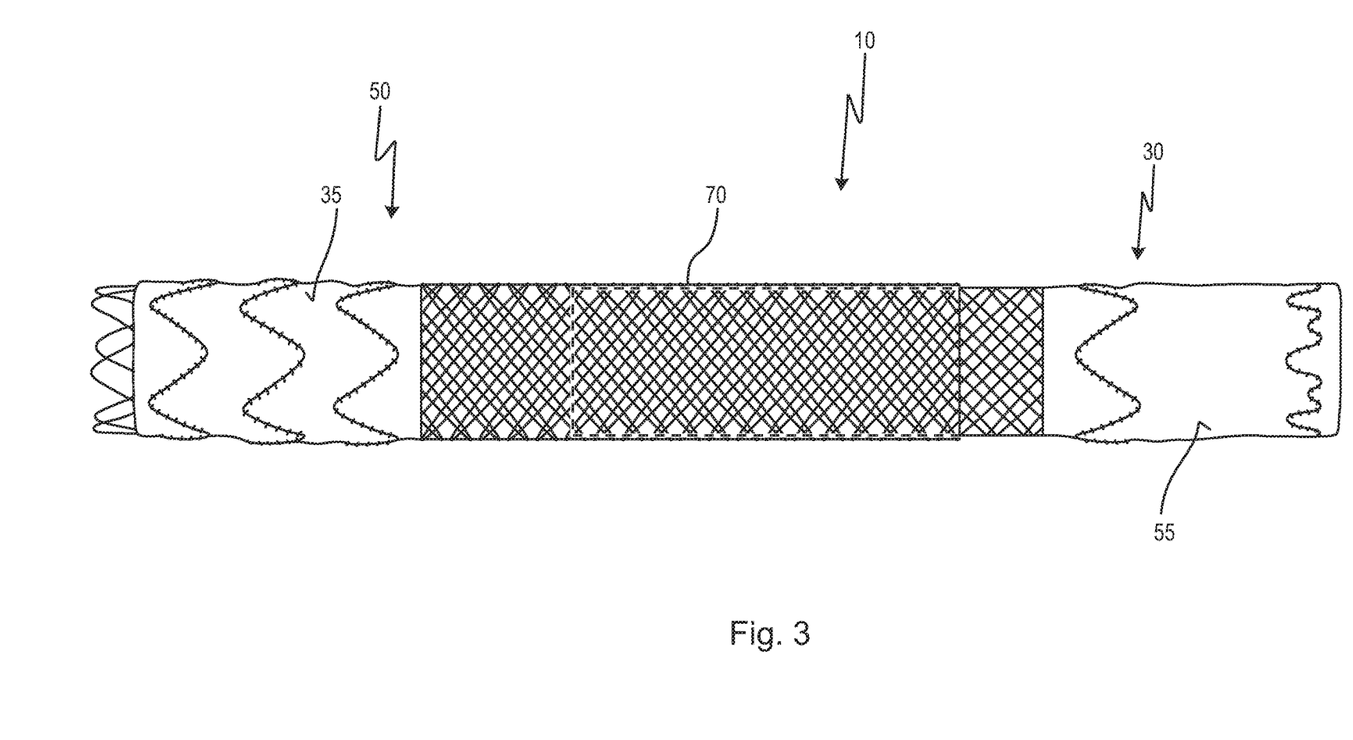
FIG. 3: shows a schematic representation of the assembled stent-graft system, in which the stent portion of the first stent-graft body and the stent portion of the second stent-graft body overlap and are partially inserted into each other.

FIG. 3 shows the assembled or partially mutually-inserted form of the stent-graft system 10, wherein not all the reference numerals used in the present case for descriptive purposes in FIGS. 1 and 2 are shown again, for reasons of clarity.

As shown in FIG. 3, the first stent-graft body 30 has been inserted via its second stent-graft-body end 33, or, more specifically, via its second stent-portion end 24, partially with its stent portion 38, into the stent portion 58 of the second stent-graft body 50 via its second stent-portion end 64, and therefore the two stent portions 38 and 58 partially overlap and thereby form one shared stent portion 70. In the expanded state, the two stent portions 38, 58 become anchored due to the outwardly directed radial force which is exerted outwardly by the internally guided stent portion 38 and, therefore, in the direction of the stent portion 58 which, in turn, presses against a vessel wall and fixes the system 10 in the vessel to be treated.

Figure 4:
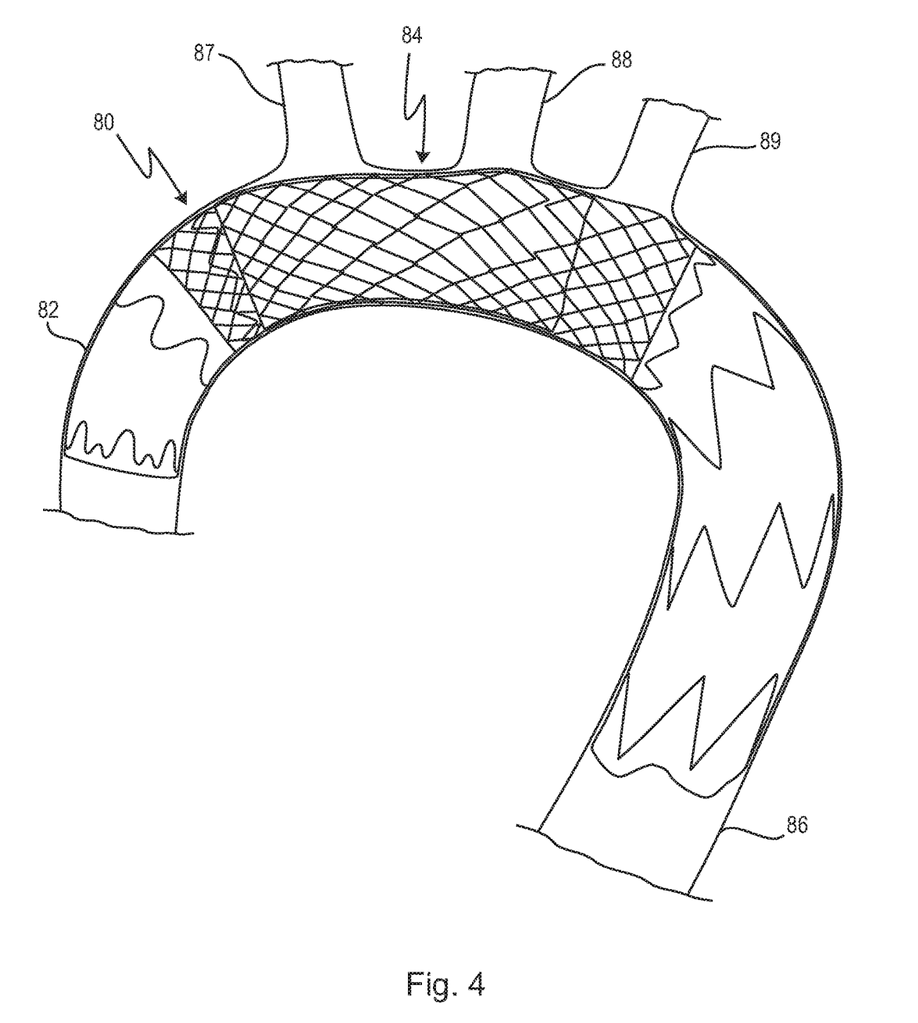
FIG. 4: shows a schematic representation of the stent-graft system assembled as in FIG. 3, positioned and released in the aortic arch.

Finally, FIG. 4 shows the embodiment of the stent-graft system 10 according to the invention—which has been assembled as in FIG. 3—in a state in which it has been introduced into an aorta 80 and has been expanded there: In FIG. 3, reference numeral 82 indicates one part of the ascending aorta, reference numeral 84 indicates the aortic arch, and reference numeral 86 indicates the descending aorta. As is evident from FIG. 3, three vessels 87, 88 and 89 branch off in the region of the aortic arch 84, namely the Truncus brachiocephalus 87, the Arteria carotis communis 88, and the Arteria subclavia sinistra 89.

FIG. 4 further shows the position or positioning of the assembled embodiment of the stent-graft system 10 according to the invention, which is represented in FIG. 3: It is evident that the stent-graft portion 34 of the first stent-graft body 30 is positioned proximally to the Truncus brachiocephalus, and furthermore the shared stent portion 70—which has been assembled from the two stent portions 38, 58 and is free from prosthesis material—has been released in the aortic arch 84 and can supply blood, via its cells or openings or meshes 40, to the branching-off vessels 87, 88 and 89. The stent-graft portion 54 of the second stent-graft body 50 is positioned distally to the Arteria subclavia sinistra 89.

In order to deliver the stent-graft system 10 according to the invention, the stent-graft bodies 30, 50 are loaded onto a delivery system (not shown) and are held in a compressed state via a suitable sleeve (not shown). Methods and devices for delivering vascular prostheses are commonly known to a person skilled in the art from the prior art. The stent-graft body 50, which is held in the compressed state, is initially advanced into the descending aorta until the entire stent-graft portion 54 of the second stent-graft body 50 lies distally to the Arteria subclavia. The correct placement can be controlled, for example, via suitable, e.g., radiopaque, markers provided on the stent-graft body 50. After correct placement, the stent-graft body 50 can be released by withdrawing the sleeve, wherein, after the stent-graft portion 54 of the stent portion 58 which is free from prosthesis material, i.e., is not covered, is released in the aortic arch 84, wherein the openings or meshes 40 are so spacious that there is no danger in the sense of obstructing the branches to the head-neck vessels 87, 88 and 89 (Truncuns brachiocephalicus, left Aorta carotis communis, left Arteria subclavia).

In a subsequent step, the first stent-graft body 30, in the compressed state, is at least partially advanced, via its stent portion 38, into the expanded stent portion 58 of the second stent-graft body 50, and the stent-graft body 30 is released in the vessel, by withdrawing the compressed sleeve, in such a way that the stent portion 38 becomes anchored in the stent portion 58, and the stent-graft portion 54 comes to rest proximally to the branch to the Truncus brachiocephalicus 87.

It becomes clear to a person skilled in the art that he can ascertain and specifically implement the exact dimensions and spatial requirements of the individual stent-graft-body portions, i.e., the stent-graft portion 34, 54 and the stent portions 38, 58, by performing a preliminary examination of the patient to be treated.

What is claimed is:

1. A method for releasing a stent-graft system, wherein the stent-graft system comprises:
a first hollow cylindrical stent-graft body and
at least one second hollow cylindrical stent-graft body,
wherein the first and the second stent-graft bodies are two structurally separate stent-graft bodies, and
wherein the first and the second stent-graft bodies each have a first end, a second end, and a longitudinal axis, wherein the first and the second stent-graft bodies each comprise a stent-graft portion which is formed from a stent-graft scaffold and a prosthesis material fixed thereto,
wherein the first and the second stent-graft bodies each further comprise a stent portion which is formed from a stent scaffold which is free from prosthesis material and comprises a first and a second stent-portion end, wherein the stent portion is fixedly connected via its first stent-portion end to the stent-graft portion in each case, and wherein the stent portion of the first stent-graft body and the stent portion of the second stent-graft body are designed in such a way that they can be at least partially inserted into one another via their respective second stent-portion ends in order to form one shared stent portion which is free from prosthesis material, and
said method for releasing the stent-graft system comprises the following steps:
inserting the first stent-graft body into an aorta of a patient in the compressed state in such a way that the stent-graft portion of the first stent-graft body is positioned completely distally to the Arteria subclavia;
transferring the first stent-graft body into the expanded state in such a way that the stent portion of the first stent-graft body that is free from prosthesis material is released in the aortic arch in the region of the branches to the Truncus brachiocephalus, the Arteria carotis communis, and the Arteria subclavia sinistra,
inserting the second stent-graft body into the aorta of a patient in the compressed state in such a way that the stent-graft portion of the second stent-graft body is positioned completely proximally to the branch to the Truncus brachiocephalus, and the stent portion of the second stent-graft body that is free from prosthesis material is at least partially inserted into the stent portion of the first stent-graft body that is free from prosthesis material; and transferring the second stent-graft body into the expanded state in such a way that the stent portion of the second stent-graft body that is free from prosthesis material is at least partially anchored in the stent portion of the first stent-graft body that is free from prosthesis material.

2. The method as claimed in claim 1, wherein the scaffold of the stent-graft portion of the first and/or the second stent-graft body is formed from stent springs which are successively arranged at a distance over its longitudinal direction and which circumferentially meander, and comprises a prosthesis material which is fastened to the stent springs and connects said stent springs.

3. The method as claimed in claim 1, wherein the stent-graft system as claimed in claim 1, wherein the scaffold of the stent-graft portion and of the stent portion of the first and/or second stent-graft body are formed as one piece, and the prosthesis material in the stent-graft portion is applied thereon as coating foil.

4. The method as claimed in claim 1, wherein the prosthesis material comprises a material which is selected from a textile or a polymer.

5. The method as claimed in claim 1, wherein the prosthesis material comprises a material or is formed from said material, which is selected from polyester, polyurethane, polystyrene, polytetrafluorethylene, ultra-high molecular-weight polyethylene (UHMPE), or mixtures thereof.

6. The method as claimed in claim 1, wherein the stent-graft system is designed for implantation into an aorta, in particular in the region of the ascending aorta, the aortic arch, and the descending aorta, wherein the stent-graft system can be transferred from a compressed state into an expanded state for insertion into the aorta, and wherein the first and the second stent-graft bodies are designed for anchoring the stent-graft system in the aorta.

7. The method as claimed in claim 1, wherein the stent-graft portion and the stent portion of the first and/or second stent-graft body is made from a self-expanding material or comprises such a material.

8. The method as claimed in claim 1, wherein the shared stent portion which is free from prosthesis material can be released in the expanded state in the region of the aortic arch.

9. The method as claimed in claim 1, wherein the stent-graft portion of the first and/or second stent-graft body each comprises between two and five circumferentially meandering stent springs.

10. The method as claimed in claim 1, wherein the stent portion of the first and/or second stent-graft body that is free from prosthesis material comprises a woven or twisted wire mesh.

11. The method as claimed in claim 1, the stent portion of the first and/or second stent-graft body that is free from prosthesis material is a laser-cut tube.

12. A method for treating a dissection or an aneurysma of a patient in need thereof, wherein the method comprising the steps of introducing and releasing a stent-graft system in a patient's blood vessel wherein the dissection or aneurysma is contained, in particular into the thoracic aorta, wherein the stent-graft system comprises:
a first hollow cylindrical stent-graft body and
at least one second hollow cylindrical stent-graft body,
wherein the first and the second stent-graft bodies are two structurally separate stent-graft bodies, and
wherein the first and the second stent-graft bodies each have a first end, a second end, and a longitudinal axis, wherein the first and the second stent-graft bodies each comprise a stent-graft portion which is formed from a stent-graft scaffold and a prosthesis material fixed thereto,
wherein the first and the second stent-graft bodies each further comprise a stent portion which is formed from a stent scaffold which is free from prosthesis material and comprises a first and a second stent-portion end, wherein the stent portion is fixedly connected via its first stent-portion end to the stent-graft portion in each case, and wherein the stent portion of the first stent-graft body and the stent portion of the second stent-graft body are designed in such a way that they can be at least partially inserted into one another via their respective second stent-portion ends in order to form one shared stent portion which is free from prosthesis material, and
wherein the releasing comprises the steps of:
inserting the first stent-graft body into an aorta of a patient in the compressed state in such a way that the stent-graft portion of the first stent-graft body is positioned completely distally to the Arteria subclavia;
transferring the first stent-graft body into the expanded state in such a way that the stent portion of the first stent-graft body that is free from prosthesis material is released in the aortic arch in the region of the branches to the Truncus brachiocephalus, the Arteria carotis communis, and the Arteria subclavia sinistra,
inserting the second stent-graft body into the aorta of a patient in the compressed state in such a way that the stent-graft portion of the second stent-graft body is positioned completely proximally to the branch to the Truncus brachiocephalus, and the stent portion of the second stent-graft body that is free from prosthesis material is at least partially inserted into the stent portion of the first stent-graft body that is free from prosthesis material; and
transferring the second stent-graft body into the expanded state in such a way that the stent portion of the second stent-graft body that is free from prosthesis material is at least partially anchored in the stent portion of the first stent-graft body that is free from prosthesis material.

13. The method as claimed in claim 12, wherein the scaffold of the stent-graft portion of the first and/or the second stent-graft body is formed from stent springs which are successively arranged at a distance over its longitudinal direction and which circumferentially meander, and comprises a prosthesis material which is fastened to the stent springs and connects said stent springs.

14. The method as claimed in claim 12, wherein the stent-graft system as claimed in claim 1, wherein the scaffold of the stent-graft portion and of the stent portion of the first and/or second stent-graft body are formed as one piece, and the prosthesis material in the stent-graft portion is applied thereon as coating foil.

15. The method as claimed in claim 12, wherein the prosthesis material comprises a material which is selected from a textile or a polymer.

16. The method as claimed in claim 12, wherein the prosthesis material comprises a material or is formed from said material, which is selected from polyester, polyurethane, polystyrene, polytetrafluorethylene, ultra-high molecular-weight polyethylene (UHMPE), or mixtures thereof.

17. The method as claimed in claim 12, wherein the stent-graft system is designed for implantation into an aorta, in particular in the region of the ascending aorta, the aortic arch, and the descending aorta, wherein the stent-graft system can be transferred from a compressed state into an expanded state for insertion into the aorta, and wherein the first and the second stent-graft bodies are designed for anchoring the stent-graft system in the aorta.

18. The method as claimed in claim 12, wherein the stent-graft portion and the stent portion of the first and/or second stent-graft body is made from a self-expanding material or comprises such a material.

19. The method as claimed in claim 12, wherein the shared stent portion which is free from prosthesis material can be released in the expanded state in the region of the aortic arch.

20. The method as claimed in claim 12, wherein the stent-graft portion of the first and/or second stent-graft body each comprises between two and five circumferentially meandering stent springs.

21. The method as claimed in claim 12, wherein the stent portion of the first and/or second stent-graft body that is free from prosthesis material comprises a woven or twisted wire mesh.

22. The method as claimed in claim 12, the stent portion of the first and/or second stent-graft body that is free from prosthesis material is a laser-cut tube.

* * * * *